United States Patent [19]

Zennaro et al.

[11] Patent Number: 5,856,365
[45] Date of Patent: Jan. 5, 1999

[54] PROCESS FOR THE PREPARATION OF A CATALYST USEFUL FOR THE CONVERSION OF SYNTHESIS GAS

[75] Inventors: Roberto Zennaro; Andrea Gusso, both of Venice; Mario Gabriele Clerici, San Donato Milanese, all of Italy

[73] Assignees: Agip Petroli S.p.A., Rome, Italy; Institut Francais du Petrole, Rueil-Malmaison, France

[21] Appl. No.: 684,378

[22] Filed: Jul. 19, 1996

[30] Foreign Application Priority Data

Aug. 4, 1995 [IT] Italy .................................. MI95A1726
Apr. 11, 1996 [IT] Italy .................................. MI96A0691

[51] Int. Cl.[6] .................................................. C07C 27/00
[52] U.S. Cl. ........................ 518/715; 502/327; 518/700; 518/717
[58] Field of Search .................................... 518/700, 717; 502/327; 515/715

[56] References Cited

U.S. PATENT DOCUMENTS

| | | |
|---|---|---|
| 4,088,671 | 5/1978 | Kobylinski . |
| 4,413,064 | 11/1983 | Beuther et al. . |
| 4,493,905 | 1/1985 | Beuther et al. . |
| 4,822,824 | 4/1989 | Iglesia et al. . |

OTHER PUBLICATIONS

"Advances in Catalysis", vol. 30, pp. 165–171, (Academic Press, NY 1981).
"The Fischer Tropsch and Related Synthesis", (John Wiley & Son, Inc., New York, 1951); pp. 114–141.
"Catalysis", vol. IV, (P.H. Emmet ed., Reinhold, New York), pp. 344–371.

*Primary Examiner*—Michael L. Shippen
*Attorney, Agent, or Firm*—Kramer Levin Naftalis & Frankel; George P. Hoare, Jr.

[57] ABSTRACT

Process for the preparation of a catalyst including an inert support, cobalt, ruthenium and a third element selected from scandium and yttrium, comprising at least the following steps:

1) Preparation of a first catalytic precursor (A) containing cobalt and the inert support: subsequent calcination, reduction and passivation;

2) Preparation of a second catalytic precursor (B) containing cobalt, ruthenium and the inert support, by means of the deposition of ruthenium on the first catalytic support (A): subsequent calcination, reduction and passivation 3) Preparation of the final catalyst by means of the deposition of an element selected from scandium and yttrium on the catalytic precursor (B); subsequent calcination, reduction and passivation.

6 Claims, No Drawings

PROCESS FOR THE PREPARATION OF A CATALYST USEFUL FOR THE CONVERSION OF SYNTHESIS GAS

This invention relates to a process for the preparation of a catalyst and its use in the conversion of synthesis gas according to the FISCHER TROPSCH process, that is in the preparation of mainly liquid hydrocarbons starting from mixtures of CO and $H_2$.

More in details, the subject of this invention is a process for the preparation of a catalyst, essentially consisting of Co, Ru and a third element, selected from scandium and yttrium, said catalyst being supported on an inert support.

The choice of cobalt is due to the fact that this latter favours the formation of saturated products with high molecular weight at a lower temperature in comparison, for instance, with iron based systems.

The use of cobalt based catalysts goes back to the first works of Fischer in 1932 (H. H. Storch, N. Golumbic, R. B. Anderson, "The Fischer Tropsch and Related Synthesis", John Wiley & Son, Inc., New York, 1951), who developed the system $Co/ThO_2/MgO$/kieselguhr.

Afterwards, the evolution of such systems led to the identification of various promoters to be joined to cobalt in order to increase the selectivity to hydrocarbons with high molecular weight, and this occurred mainly during the last twenty years. In fact the price increase of the crude in the '70s stimulated the exploration of other ways for the production of liquid fuels and chemicals.

U.S. Pat. No. 4,088,671 describes a catalyst for Fischer-Tropsch having, as active ingredients, cobalt and ruthenium, the first of which present in greater quantity than the second.

U.S. Pat. No. 4,413,064 describes a catalyst for a fixed bed reactor mainly formed by cobalt, ruthenium and thorium or lanthanum oxide, supported on alumina, prepared through impregnation of alumina with a water solution of a cobalt salt and a following non-water organic impregnation of a ruthenium salt and a salt of a metal belonging to the Group IIIB or IVB. Among the metals of these groups, U.S. '064 lists also scandium, yttrium, even though the preferred metals are thorium and lanthanum.

The above mentioned catalyst is particularly effective in the conversion of the synthesis gas in order to give a hydrocarbon product with high paraffin contents, having the boiling point in the field of diesel fuel, that is C9–C21. U.S. '064 does not give any information about the capability of the described catalysts to produce heavier hydrocarbons, a preferable process in comparison with the process that produces hydrocarbons with a boiling point in the range of the diesel fuel.

A process has now been found for the preparation of a catalyst supported on a inert material, said catalyst essentially consisting of a major amount of cobalt and a minor amount of ruthenium and of a third element selected from scandium and yttrium, particularly effective in the conversion of the synthesis gas to hydrocarbon products containing noticeable quantities of hydrocarbons having a number of carbon atoms greater than or equal to 22.

According to this, this invention relates to a process for the preparation of a catalyst essentially consisting of an inert support selected from at least one oxide of at least one element selected from Si, Ti, Al, Zr, Zn, Mg, Sn, preferably silicon and, in the form of elements or in the form of oxides, a major amount of cobalt and a minor amount of ruthenium and of a third element selected from scandium and yttrium, characterized by the fact that it includes at least the following steps:

1. Preparation of a first catalytic precursor (A) containing cobalt and at least part of the inert support, by means of deposition of cobalt on the inert support: subsequent calcination, reduction and passivation of the inert support containing cobalt;

2. Preparation of a second catalytic precursor (B) containing cobalt, ruthenium and at least part of the inert support, by means of the deposition of ruthenium on the first catalytic precursor (A): subsequent calcination, reduction and passivation of the inert support containing cobalt and ruthenium;

3. Preparation of the final catalyst by means of the deposition of an element selected from scandium and yttrium on the catalytic precursor (B); subsequent calcination, reduction and passivation of the inert support containing cobalt, ruthenium and the third element.

A further object of this invention consists of the catalyst that can be obtained according to the above described process.

In the process of the present invention, the step 1 consists of an initial deposition of cobalt on at least a part of the inert support, preferably on the whole inert support. This deposition, as well as the deposition of ruthenium in step 2 and of the third element in step 3, can be carried out according to various techniques known to those having ordinary skill in the art, for instance through exchange, impregnation, dry impregnation (also known as incipient imbibition), precipitation, gelation and mechanical mixing. In the preferred embodiment, the deposition of cobalt in step 1 is accomplished through the technique of dry impregnation. According to this technique, the material to be impregnated is placed in contact with a volume of solution approximately equal to the volume of the pores.

In step 1, it is preferable to use aqueous solutions of cobalt salts. Cobalt salts of any type can be used as cobalt salts, for instance halides, nitrate, acetate, oxalate, sulphate, the complex formed with oxalic acid and oxalates, the complex formed with lactic acid and lactates, the complex formed with tartaric acid and tartrates, the complex formed with another polyacid or hydroxiacid and the related salts, the complex formed with acetylacetonates.

After deposition on the inert support of the desired quantity of cobalt salt, preferably of cobalt nitrate, a step of calcination follows and then a step of reduction and then a step of passivation. Optionally, before calcination the impregnated support is submitted to drying in order to remove most water. This drying can be made at first at temperatures between 10° and 30° C. and afterwards at temperatures between 100° and 120° C., preferably operating in the presence of gas stream.

In step 1, the calcination is made at a temperature between 300° C. and 500° C., preferably between 350° C. and 450° C., in an air environment in order to remove all organic residues.

The product calcined in this way is then submitted to a step of reduction in an environment mainly constituted of hydrogen, at a temperature between 300° and 500° C., preferably between 350° and 450° C. It is preferable to gradually bring the material to be calcinated at this temperature, for instance at a heating velocity between 3° and 20° C./minute. Usually, the reduction step is terminated, at the above mentioned temperature, in a period of time between 10 and 20 hours and with a $H_2$ flow between 1 and 3 liters/hour for a gram of catalyst. At the end of the reduction step, a passivation step follows in presence of oxygen diluted with an inert gas, generally nitrogen, preferably carried out at a temperature between 10° C. and 80° C. Using, for instance, nitrogen containing 1–2% of $O_2$ (flow of 2 liters/hour), said step could last between 1 and 5 hours at 25° C.

It is evident that at the end of the reduction (and obviously before the passivation) the sample must be cooled.

The second step of the process of this invention consists in depositing ruthenium on the catalytic precursor (A) obtained at the end of step 1.

Unlike step 1, in this case it is preferable to deposit the ruthenium by means of the impregnation technique, using organic solutions of ruthenium salts. For instance, it is possible to use ruthenium nitrate dissolved in acetone and/or ethanol.

As in step 1, after depositing the ruthenium, a step of calcination follows, and then a step of reduction and a step of passivation. In this case, however, it is preferable to carry out the calcination step at a slightly lower temperature than the temperature of calcination in step 1, that is between 200° and 400° C., preferably between 250° C. and 350° C. The reduction and the passivation are instead carried out at the same conditions of temperature of step 1.

At the end of the second reaction step the catalytic precursor (B) is obtained, mainly formed by cobalt and ruthenium deposited on the inert support.

The third and last step of the process of this invention consists in depositing on the precursor (B), obtained at the end of the second step, a third element selected from yttrium and scandium. In one embodiment, a scandium or yttrium nitrate is used, dissolved in a solvent selected from acetone, lower alcohols, water and related mixtures. As far as calcination, reduction and passivation is concerned, the same conditions described for step 2 are used. The catalytic composition that can be obtained through the process of this invention contains Co (in metallic form or as derivative), Ru (in metallic form or as derivative) and at least a third additional element (still in metallic form or as derivative) selected from Sc and Y, all these elements being dispersed on a support and, if they are present as derivatives, the oxide form being the preferred one.

As previously described, said support is formed by at least an oxide selected from at least one of the following elements: Si, Ti, Al, Zr, Zn, Mg. In the preferred embodiment the inert support is silica.

The contents of said elements in the final catalyst, expressed as metals and defined as weight percentage in comparison with the weight of the catalyst, vary in the following ranges:

| Element | Range | Preferred ranges |
| --- | --- | --- |
| Co | 1–50% | 3–35% |
| Ru | 0.05–5% | 0.1–3% |
| Third | 0.5–5% | 0.1–3% |

As already written, this invention relates also to a process for the preparation of hydrocarbons of the synthesis gas in presence of the above described catalytic system.

As far as the Fischer-Tropsch synthesis is concerned, this can be considered as the hydrogenation process of the carbon monoxide in order to produce higher hydrocarbons with a mainly linear chain. In the Fischer-Tropsch synthesis, the selectivities of the hydrocarbon products are determined by the capacity of the catalyst to favour the propagation reaction of the hydrocarbon chain with respect to the termination chain.

The distribution of hydrocarbon products can be described through the "polymerization" type growth mechanism elaborated by Schultz and Flory (P. Biloen, W. M H. Sachtler, Advance in Catalysis, vol. 30, pages 169–171, Academic Press, New York, 1981) and adapted to the synthesis considered by Anderson (R. B. Anderson, Catalysis, vol. IV, P. H. Emmet ed., Reinhold, New York, 1956). The model called Anderson-Schultz-Flory (ASF) is elaborated on statistical bases in relation to the probability of chain growth, alfa (a), and imposes three conditions:
1. The growth of the chain must take place by addition of intermediate species with only one carbon atom;
2. The termination must take place through simple desorption from the chain, e. g. hydrogen extraction;

The growth factor is independent from the length of the chain.

The mathematical representation is the following:

$$W_n = (1-\alpha)^2 \cdot \alpha^{[n-1]}$$

where n is the number of carbon atoms in the product, $W_n$ is the weight fraction of the product and alfa ($\alpha$) the growth factor, which can have values between 0 and 1.

From the expression in a logarithmic form:

$$\log W_n/n = n\log\alpha + \log[(1-\alpha)^2/\alpha]$$

it is possible to achieve alfa as the slope of the linear ratio between $\log W_{n/n}$ and n.

The values of the growth factor alfa are affected both by the reaction conditions and by the composition of the catalyst. In general, a lowering in the reaction temperature causes an increase of the selectivity to liquid hydrocarbons ($C_5$) but an unavoidable decrease of the conversion of syngas (conv. CO). There are therefore selectivity and conversion limits, caused by economic considerations that impose precise practicability fields to the reaction conditions to be used. It is possible to exceed such limits with the use of catalytic systems particularly selective towards hydrocarbon fractions with high molecular weight (for instance $C_{25+}$), already at low temperatures.

This invention relates therefore to a catalytic composition that allows to convert the CO and $H_2$ mixture, known as synthesis gas, in essentially saturated and linear hydrocarbons, having a percentage of $C_{25+}$ between 22.5 and 31% weight and with values of the growth factor alfa greater than 0.90.

The operative conditions of such catalysts are, in their turn, the conditions known in the state of art for the Fischer-Tropsch synthesis.

The conversion of synthesis gas to hydrocarbons takes place at a pressure usually between 0.1 and 15 Mpa, preferably between 1 and 10 Mpa, at a temperature usually in the range between 150° C. and 350° C., preferably between 170° and 300°.

The space velocity per hour is usually between 100 and 20000, preferably between 400 and 5000, volume of synthesis gas per volume of catalyst and per hour; the ratio $H_2/CO$ in the synthesis gas is usually between 1:2 and 5:1, preferably between 1.2:1 and 2.5:1.

The catalyst can be used in the form of fine powder (approximately 10–700 $\mu$m) or as particles having an equivalent diameter between 0.7 and 10 mm, respectively in presence of a liquid phase (in operative conditions) and of a gaseous phase, or of a gaseous phase. The liquid phase may consist of at least one hydrocarbon having at least 5, preferably at least 10, carbon atoms per molecule. In the preferred embodiment, the liquid phase is essentially formed by the same reaction product.

As an example, it can be reminded that the catalysts according to this invention can be used in a fixed bed reactor, continuously fed with a mixture of CO and $H_2$ and operating at the following conditions:

| | |
| --- | --- |
| reaction temperature | 200–215° C. |
| reaction pressure | 20 bar |
| space velocity | 500 h-1 |
| mixture $H_2$/CO | 2/1 |

The catalysts prepared in the examples between 1 and 6 with the compositions summarized in Table 1, were evaluated in these conditions. The results of the reactivity tests are reported in Table 2.

EXAMPLE 1

Catalyst A (Reference)

Silica is used with a surface area of 300 m$^2$/g, specific volume of the pores of 1.3 cm$^3$/g, diameter of the particles of 20 μm and specific gravity of 0.388 g/cc.

Said silica is dry impregnated with a nitric solution of Co(NO$_3$)$_2$.6H$_2$O in two following steps, separated by a drying at 120° C. for 16 hours, in such quantities as to obtain a Co percentage equal to 15% in weight with reference to the total catalyst. The silica impregnated in this way is calcinated at 400° C. in air for 4 hours, and then treated in a stream of H$_2$ at a space velocity (GHSV) of 1000 h$^{-1}$ within a tubular reactor at 400° C. for 16 hours. The sample so reduced is passivated in mixture (1%) O$_2$/(99%)N$_2$ with GHSV at 1000 h$^{-1}$ for 2 hours at room temperature.

On the monometallic sample CO/SiO$_2$ a solution 7.5 10$^{-3}$M of Ru(NO$_3$)$_3$.xH$_2$O is added, obtained by means of the following procedure: precipitation as hydroxide at pH=7.2 of RuCl$_3$. xH$_2$O, subsequent elimination of chlorides, re-solubilization in HNO$_3$ conc. and dilution in CH$_3$COCH$_3$ in ratio 1:250 v/v.

The acetone solution of ruthenium is added to the sample in such a quantity as to have 0.2% of Ru in weight with reference to the total. The slurry is left under stirring for two hours, then dried under vacuum at 40° C.

A phase of calcination in air at 300° C. for 4 hours and a reduction/passivation analogous to the one described above follow.

(Catalyst A: Co/Ru/SiO$_2$ 15% Co, 0.2% Ru)

EXAMPLE 2

Catalyst B

For the preparation of the catalyst B, a solution of Y(NO$_3$)$_3$ 10$^{-3}$M in acetone is added to 50 g of catalyst A in such volume as to obtain a final weight percentage of yttrium equal to 0.2%.

The suspension thus obtained is left stirring for two hours and then dried under vacuum at 40° C. The sample is then calcinated at 300° C. for 4 hours in air, reduced at 400° C. in H$_2$ with GHSV equal to 1000 h$^{-1}$ and passivated in (1%) O$_2$/(99%)N$_2$ with GHSV of 1000 h$^{-1}$ at room temperature.

(Catalyst B: Co/Ru/Y/SiO$_2$ 15% Co, 0.2% Ru, 0.2% Y)

EXAMPLE 3

Catalyst C

The preparation of the catalyst C differs from that described in example 2 by the use of a solution of Sc(NO$_3$)$_3$ 10$^{-3}$M in acetone in such a volume as to obtain a final weight percentage of scandium equal to 0.2%.

(Catalyst B: Co/Ru/Sc/SiO$_2$ 15% Co, 0.2% Ru, 0.2% Sc)

EXAMPLE 4

Catalyst D

The preparation of the catalyst D differs from that described in example 3 by the use of a solution of Sc(NO$_3$)$_3$ 10$^{-3}$M in acetone in such a volume as to obtain a final weight percentage of scandium equal to 0.5%.

(Catalyst D: Co/Ru/Sc/SiO$_2$ 15% Co, 0.2% Ru, 0.5% Sc)

COMPARATIVE EXAMPLE 5

Catalyst E

This catalyst is prepared according to the technique described in U.S. Pat. No. 4,413,064, example 1.

As support of the catalyst 100 grams of gamma-alumina Harshaw are used (surface area=175 m$^2$/g; average pores size=0.5 cm$^3$/g; average particle diameter=40–45 mm; purity=99%; specific gravity=0.884 g/cc) that are calcinated at 600° C. for 2 hours in an air stream.

An aqueous solution of cobalt nitrate is then prepared, dissolving 87.1 g of Co(NO$_3$)$_3$.6H$_2$O with distilled water to a final volume of 100 cc.

With the technique of the incipient wetness imbibition, the support is impregnated with this solution and, after a "digestion" for some hours, it is dried in an oven for 16 hours at 120° C.

Then an ethanole solution 0.1M of La(NO$_3$)$_3$.6H$_2$O and an acetone solution 0.00156M of Ru(NO$_3$)$_3$ are prepared. 7.2 cc of the first solution, diluted with ethanol to 33.5 cc, and 63.5 cc of the second, brought to a volume to 66.5 cc with acetone, are taken. Both of them are poured into a flask of 250 cc where 50 grams of the sample Co/Al$_2$O$_3$ are present, so that a ratio acetone/ethanol of approximately 2 and a solvent quantity are obtained equal to 2 cc per gram of support. The sample is dried with a rotating evaporator, under vacuum and with the temperature of the bath of approximately 35° C. In order to complete the removal of the solvent, the sample is left in the oven for 2 hours at 90° C.

A product is obtained with contents of Co of 15% w/w, of Ru of 0.2% w/w and of La of 0.2% w/w.

The sample prepared in this way is charged in the reactor and reduced with H$_2$ (35 l/h), according to the following thermic profile:

1. The temperature is brought from 25° to 100° C. with a velocity of 1° C./min and it is kept at 100° C. for 1 hour;
2. With the same velocity the temperature increases to 200° C., and stays at this temperature for 2 hours
3. At the end the temperature of 360° C. is reached with a velocity of 10° C./min and this temperature is maintained for 16 hours.

The temperature is then brought to 25° C. while the catalyst is left in a nitrogen stream. It is then passivated with a mixture of air (1.2 l/h) and nitrogen (60 l/h) for a period of 16 hours.

COMPARATIVE EXAMPLE 6

Catalyst F

This catalyst is prepared according to the technique described in U.S. Pat. No. 4,413,064, example 1.

As support for the catalyst 25 grams of silica are used (with the same characteristics described in example 1) that are calcinated at 600° C. for 2 hours in an air stream.

An aqueous solution of cobalt nitrate is then prepared, dissolving 21.77 g of Co(NO$_3$)$_2$.6H$_2$O with distilled H$_2$O to a volume of 45 cc.

With the technique of the incipient wetness imbibition, the support is impregnated with this solution and, after the "digestion" for some hours, it is dried for 16 hours at 120° C. in an oven.

Then an ethanole solution 0.1M of La(NO$_3$)$_3$.6H$_2$O and an acetonic solution 0.00152M of Ru(NO$_3$)$_3$ are prepared. 5.5 cc of the first solution, diluted with ethanol to 25 cc, and 50 cc of the second, are taken. Both of them are poured into a flask of 250 cc where 38 grams of the sample Co/SiO$_2$ are present, so that a 10 ratio acetone/ethanol of approximately 2 and a solvent quantity are obtained equal to 2 cc per gram of support.

The sample is dried with a rotavapor, under vacuum and with the temperature of the bath of approximately 35° C. In order to completely remove the solvent, the sample is left in the oven for 2 hours at 90° C.

The composition of the catalyst is: Co 15% w/w, Ru 0.2% w/w and La 0.2% w/w.

The sample prepared in this way is charged in the reactor and reduced with H2 (27 l/h), according to the following profile:

1. The temperature is brought from 25° to 100° C. with a velocity of 1° C./min and it is kept at 100° C. for 1 hour;

2. With the same velocity the temperature increases to 200° C., and stays at this temperature for 2 hours;
3. At the end a final temperature of 360° C. is reached with a velocity of 10° C./min and this temperature is maintained for 16 hours.

The temperature is then brought to 25° C. while the catalyst is left in a nitrogen stream. It is then passivated with a mixture of air (0.9 l/h) and nitrogen (45.6 l/h) for a period of 16 hours.

TABLE 1

| Example | Catalyst | % Co | % Ru | M | % M | Support |
|---|---|---|---|---|---|---|
| 1 comp. | A | 15 | 0.2 | — | — | $SiO_2$ |
| 2 | B | 15 | 0.2 | Y | 0.2 | $SiO_2$ |
| 3 | C | 15 | 0.2 | SC | 0.2 | $SiO_2$ |
| 4 | D | 15 | 0.2 | SC | 0.5 | $SiO_2$ |
| 5 comp. | E | 15 | 0.2 | La | 0.2 | $Al_2O_3$ |
| 6 comp. | F | 15 | 0.2 | La | 0.2 | $SiO_2$ |

TABLE 2

| | Catalyst A (comp) | | Catalyst B | | Catalyst C | | Catalyst D | | Catal.E (comp) | Catal.F (comp) |
|---|---|---|---|---|---|---|---|---|---|---|
| T (°C.) | 200 | 215 | 200 | 205 | 205 | 215 | 205 | 215 | 200 | 205 |
| Conv CO % | 51.69 | 64.96 | 72.25 | 70.12 | 66.17 | 84.12 | 71.68 | 91.43 | 72.68 | 63.86 |
| $C_2$ (g/kgh) | 86.7 | 101.3 | 98.44 | 92.0 | 96.6 | 123.4 | 108.2 | 108.6 | 102.5 | 98.78 |
| alfa | 0.83 | 0.88 | 0.93 | 0.92 | 0.93 | 0.91 | 0.91 | 0.91 | 0.89 | 0.82 |
| C1–C4 (%) | 13.59 | 22.04 | 16.5 | 21.54 | 20.9 | 16.7 | 20.25 | 20.95 | 14.44 | 17.3 |
| C10–C24 | 44.67 | 46.63 | 45.05 | 42.5 | 40.8 | 48.1 | 44.32 | 45.23 | 53.18 | 59.66 |
| $C_{25}$ | 10.31 | 22.68 | 31.2 | 26.25 | 26.93 | 22.66 | 25.86 | 24.01 | 20.56 | 6.69 |
| $C_5$ | 87.75 | 79.1 | 85.24 | 80.05 | 80.88 | 84.98 | 80.81 | 80.5 | 87.16 | 84.83 |

$CO/H_2 = \frac{1}{2}$; GHSV = 5000 $h^{-1}$; P = 20 bar

From a comparison between the catalyst without the third element (comparative catalyst A) and the catalyst according to this invention (B, C and D) it is evident that the system with three elements is more active at lower temperatures, with greater values of a and selectivity at $C_{25+}$.

The activities of the catalysts according to this invention are quite the same.

Comparing catalyst E (supported on alumina) and the catalyst according to this invention, it can be seen how the catalyst E produces lower values of a and selectivity at heavy hydrocarbons.

Finally, the comparative catalyst F (supported on silica as the catalyst according to this invention) shows a much greater decrease of the values of a and selectivity at $C_{25+}$ in comparison with the catalyst according to the present invention.

We claim:

1. A process for the preparation of a catalyst useful for the conversion of synthesis gas consisting essentially of an inert support selected from at least one oxide of least one element selected from the group consisting of Si, Ti, Al, Zr, Zn, Mg, Sn and, in the form of element s or in the form of oxides, a major amount of cobalt, a minor amount of ruthenium, and of a third element selected from the group consisting of scandium and yttrium, comprising the following steps:
   (1) preparing a first catalytic precursor (A) containing cobalt and at least part of an inert support, by depositing cobalt on the inert support, and subsequently calcinating, reducing, and passivating the inert support containing cobalt;
   (2) preparing a second catalytic precursor (B) containing cobalt, ruthenium, and at least part of an inert support, by depositing ruthenium on the first catalytic support (A), and subsequently calcinating, reducing, and passivating the inert support containing cobalt and ruthenium;
   (3) preparing a final catalyst by depositing an element selected from the group consisting of scandium and yttrium on the catalytic precursor (B), and subsequently calcinating, reducing, and passivating the inert support containing cobalt, ruthenium, and the third element.

2. The process according to claim 1, wherein the inert support is silica.

3. The process according to claim 1, wherein in step (1) cobalt is deposited on the whole inert support.

4. The process according to claim 1, wherein in step (1) calcination is carried out at a temperature between 350° C. and 450° C. and in steps (2) and (3) calcination is carried out at a temperature between 250° C. and 350° C.

5. A process for the synthesis of essentially linear and saturated hydrocarbons starting from a synthesis gas essentially constituted of CO and $H_2$, that comprises reacting the synthesis gas with a catalyst prepared according to claim 1, at a pressure between 0.1 and 15 Mpa, at a temperature between 150° C. and 350° C., at a volumetric hour velocity between 100 and 20000 volumes of synthesis gas per volume of catalyst and per hour, wherein the molar ratio $H_2$/CO in the synthesis gas is from 1:2 to 5:1.

6. The process according to claim 5, wherein the pressure is between 1 and 10 Mpa, the temperature between 170° and 300° C., the volumetric velocity per hour between 400 and 5000 volumes of synthesis gas per volume of catalyst and per hour, and the molar ratio $H_2$/CO in the synthesis gas is between 1.2:1 and 2.5:1.

* * * * *